United States Patent
Mossman et al.

(10) Patent No.: US 7,030,094 B2
(45) Date of Patent: Apr. 18, 2006

(54) IMMUNOSTIMULANT COMPOSITIONS COMPRISING AN AMINOALKYL GLUCOSAMINIDE PHOSPHATE AND QS-21

(75) Inventors: Sally Mossman, Seattle, WA (US); Lawrence Evans, Seattle, WA (US)

(73) Assignees: Corixa Corporation, Seattle, WA (US); Antigenics Inc., Lexington, MA (US)

(*) Notice: Subject to any disclaimer, the term of this patent is extended or adjusted under 35 U.S.C. 154(b) by 90 days.

(21) Appl. No.: 10/177,115

(22) Filed: Jun. 21, 2002

(65) Prior Publication Data

US 2003/0147920 A1 Aug. 7, 2003

Related U.S. Application Data

(63) Continuation-in-part of application No. 10/068,171, filed on Feb. 4, 2002.

(51) Int. Cl.
- *A61K 31/70* (2006.01)
- *A61K 45/00* (2006.01)
- *A61K 47/00* (2006.01)
- *A61K 9/00* (2006.01)

(52) U.S. Cl. .................. 514/26; 514/25; 424/278.1; 424/281.1; 424/282.1; 424/400

(58) Field of Classification Search ............. 424/278.1, 424/281.1, 282.1, 400; 514/26, 25
See application file for complete search history.

(56) References Cited

U.S. PATENT DOCUMENTS

| | | | | |
|---|---|---|---|---|
| 5,057,540 A | * | 10/1991 | Kensil et al. | ............ 424/278.1 |
| 5,750,110 A | | 5/1998 | Prieels et al. | |
| 5,972,339 A | * | 10/1999 | Walker | ............ 424/188.1 |
| 5,977,081 A | | 11/1999 | Marciani | |
| 6,080,725 A | | 6/2000 | Marciani | |
| 6,113,918 A | | 9/2000 | Johnson et al. | |
| 6,145,632 A | | 11/2000 | Momin et al. | |
| 6,146,632 A | * | 11/2000 | Momin et al. | ............ 424/184.1 |
| 6,262,029 B1 | | 7/2001 | Press et al. | |
| 6,303,347 B1 | | 10/2001 | Johnson et al. | |
| 6,355,257 B1 | | 3/2002 | Johnson et al. | |

FOREIGN PATENT DOCUMENTS

| | | | |
|---|---|---|---|
| WO | WO 98/50399 | * | 11/1998 |
| WO | WO 98/57659 | | 12/1998 |
| WO | WO 99/62647 | | 10/1999 |
| WO | WO 01/78777 | | 10/2001 |

OTHER PUBLICATIONS

U.S. Appl. No. 10/068,171, filed Feb. 4, 2002: Mossman et al., Immunostimulant Compositions Comprising Aminoalkyl Glocosaminide Phosphates and Saponins (copending application; not yet published).

U.S. Appl. No. 10/068,475, filed Feb. 4, 2002: Mossman et al., Immunostimulant Compositions Comprising Aminoalkyl Glocosaminide Phosphates and Saponins (copending application; not yet published).

Wijburg et al., The Role of Macrophages in the Induction and Regulation of Immunity Elecited by Exogenous Antigens; Eur. J. Immunol. 28: 479 (1998).

Jones et al., Immunization with Human Immunodeficiency Virus Type 1 rgp120$_{W61D}$ in QS21/MPL Adjuvant . . . ; J. Infect. Diseases 179: 558 (1999).

Mioore et al., The Adjuvant Combnation Mononphosphoryl Lipid A and QS21 switches T cell responses . . . ; Vaccine 17: 2517 (1999).

McCormack et al., A Phase I Trial in Negative Healthy Volunteers . . . ; Vaccine 18: 1166 (2000).

Gerard et al., Therapeutic Potential of OProtein and Adjuvant Vaccinations on Tumor Growth; Vaccine 19: 2583 (2001).

Johnson et al., Synthesis and Biolgical Evaluation of a New Class of Vaccine Adjuvants: Aminoalkyl Glucosaminide 4–Phosphates (AGPs): Bioorganic & Medicinal Chemistry Letters 9: 2273 (1999).

* cited by examiner

*Primary Examiner*—Shengjun Wang
(74) *Attorney, Agent, or Firm*—Townsend and Townsend amd Crew LLP

(57) ABSTRACT

The invention provides pharmaceutical compositions, particularly vaccine compositions, employing an adjuvant system comprising RC-529 (an aminoalkyl glucosaminide phosphate compound) and QS-21 (a saponin). Such compositions synergistically enhance the immune response in a mammal to a co-administered antigen. Also provided are methods of using the compositions in the treatment of various human diseases, including cancer, microbial infections and autoimmune disorders.

27 Claims, No Drawings

IMMUNOSTIMULANT COMPOSITIONS COMPRISING AN AMINOALKYL GLUCOSAMINIDE PHOSPHATE AND QS-21

CROSS-REFERENCES TO RELATED APPLICATIONS

This application is a continuation-in-part of application Ser. No. 10/068,171 filed Feb. 4, 2002, the disclosure of which is incorporated herein in its entirety for all purposes.

FIELD OF THE INVENTION

The present invention relates generally to vaccine formulations, to methods for their production and to their use in prophylactic and/or therapeutic vaccination. More particularly, the present invention relates to an adjuvant system comprising QS-21 in combination with an aminoalkyl glucosaminide phosphate comprising 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyoxytetradecanoylamino]-β-D-glucopyranoside triethylammonium salt.

BACKGROUND OF THE INVENTION

Humoral immunity and cell-mediated immunity are the two major branches of the mammalian immune response. Humoral immunity involves the generation of antibodies to foreign antigens. Antibodies are produced by B-lymphocytes. Cell-mediated immunity involves the activation of T-lymphocytes which either act upon infected cells bearing foreign antigens or stimulate other cells to act upon infected cells. Both branches of the mammalian immune system are important in fighting disease. Humoral immunity is the major line of defense against bacterial pathogens. In the case of viral disease, the induction of cytotoxic T lymphocytes (CTLs) appears to be crucial for protective immunity. Thus, an effective vaccine preferably stimulates both branches of the immune system to protect against disease.

Vaccines present foreign antigens from disease causing agents to a host so that the host can mount a protective immune response. Often, vaccine antigens are killed or attenuated forms of the microbes which cause the disease. The presence of non-essential components and antigens in these killed or attenuated vaccines has encouraged considerable efforts to refine vaccine components including developing well-defined synthetic antigens using chemical and recombinant techniques. The refinement and simplification of microbial vaccines, however, has led to a concomitant loss in potency. Low-molecular weight synthetic antigens, though devoid of potentially harmful contaminants, are often not sufficiently immunogenic by themselves. These observations have led investigators to add immune system stimulators known as adjuvants to vaccine compositions to potentiate the activity of the vaccine components.

Immune adjuvants are compounds which, when administered to an individual or tested in vitro, increase the immune response to an antigen in a subject to which the antigen is administered, or enhance certain activities of cells from the immune system. A number of compounds exhibiting varying degrees of adjuvant activity have been prepared and tested (see, for example, Shimizu et al. 1985, Bulusu et al. 1992, Ikeda et al. 1993, Shimizu et al. 1994, Shimizu et al. 1995, Miyajima et al. 1996). However, these and other prior adjuvant systems often display toxic properties, are unstable and/or have unacceptably low immunostimulatory effects.

Presently, the only adjuvant licensed for human use in the United States is alum, a group of aluminum salts (e.g., aluminum hydroxide, aluminum phosphate) in which vaccine antigens are formulated. Particulate carriers like alum reportedly promote the uptake, processing and presentation of soluble antigens by macrophages. Alum, however, is not without side-effects and is unfortunately limited to humoral (antibody) immunity only.

The discovery and development of effective adjuvant systems is essential for improving the efficacy and safety of existing and future vaccines. Thus, there is a continual need for new and improved adjuvant systems, particularly those that drive both effector arms of the immune system, to better facilitate the development of a next generation of synthetic vaccines. The present invention fulfills these and other needs.

SUMMARY OF THE INVENTION

In a first aspect of the present invention, there is provided an immunostimulant composition comprising QS-21 and RC-529, typically in the form of a stable emulsion or an aqueous formulation.

In another aspect of the invention, there are provided vaccine compositions comprising the above immunostimulant compositions in combination with at least one antigen. The antigens may be derived from any of a variety of sources, and will most typically be derived from a bacterium or virus, or may be derived from antigens associated with cancer, autoimmune disorders, or a number of other mammalian diseases.

In another aspect of the present invention, there is provided a method of treating a mammal suffering from or susceptible to a pathogenic infection, cancer or an autoimmune disorder comprising administering to the mammal an effective amount of a composition of the subject invention.

In another aspect of the present invention, a method is provided for enhancing the immune response in a mammal which comprises administering to the mammal a composition of the subject invention.

In another aspect of the present invention, a method is provided for enhancing the immune response in a mammal which comprises administering to the mammal a composition of the subject invention in combination with one or more antigens.

In another aspect of the invention, there are provided immunostimulant compositions comprising QS-21 and RC-529 in an aqueous formulation comprising one or more phospholipid surfactants.

DETAILED DESCRIPTION OF THE INVENTION

Aminoalkyl glucosaminide phosphate (AGP) compounds generally comprise a 2-deoxy-2-amino-α-D-glucopyranose (glucosaminide) in glycosidic linkage with an aminoalkyl (aglycon) group. AGP compounds, and methods for their synthesis and use, are described generally in U.S. Pat. No. 6,113,918 (which issued from U.S. patent application Ser. No. 08/853,826), WO 98/50399, U.S. patent application Ser. Nos. 09/074,720 and 09/439,839, and Johnson et al. (1999) Bioorg. Med. Chem. Lett. 9: 2273–2278, the disclosures of which are incorporated herein by reference in their entireties.

The AGP compound of the subject invention, referred to as RC-529, can be described structurally by Formula I below:

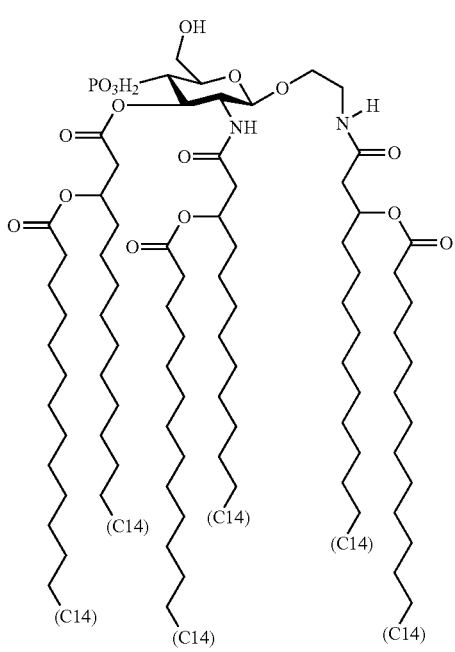

(I)

and pharmaceutically acceptable salts thereof.

One particularly preferred RC-529 compound is a 2-[(R)-3-tetradecanoyloxytetradecanoylamino]ethyl 2-deoxy-4-O-phosphono-3-O-[(R)-3-tetradecanoyoxytetradecanoyl]-2-[(R)-3-tetradecanoyoxytetradecanoylamino]-β,-D-glucopyranoside triethylammonium salt.

The QS-21 saponin employed in the vaccine compositions of the present invention can be purified from *Quillaja saponaria* Molina bark, as described in U.S. Pat. No. 5,057,540, the disclosure of which is incorporated herein by reference in its entirety. Briefly, aqueous extracts of *Quillaja saponaria* Molina bark are dialyzed against water and the dialyzed extract is lyophilized to dryness, extracted with methanol, and the methanol-soluble extract is further fractionated on silica gel chromatography and by reverse phase high pressure liquid chromatography (RP-HPLC). The individual saponins can then be separated by reverse phase HPLC. At least 22 peaks (denominated QA-1 to QA-22, also referred to herein as QS-1 to QS-21) are separable using this approach, with each peak corresponding to a carbohydrate peak and exhibiting a single band on reverse phase thin layer chromatography. The individual components can be specifically identified by their retention times on a C4 HPLC column, for example.

The substantially pure QS-21 saponin is characterized as having immune adjuvant activity, containing about 22% carbohydrate (as assayed by anthrone) per dry weight, having a UV absorption maxima of 205–210 nm, a retention time of approximately 51 minutes on RP-HPLC on a Vydac $C_4$ column having 5 μm particle size, 330 angstrom pore, 4.6 mm ID×25 cm L in a solvent of 40 mM acetic acid in methanol/water (58/42; v/v) at a flow rate of 1 ml/min, eluting with 69 to 70% methanol from a Vydac $C_4$ column having 5 μm particle size, 330 angstrom pore, 10 mm ID×25 cm L in a solvent of 40 mM acetic acid with gradient elution from 50 to 80% methanol, with a critical micellar concentration of about 0.03% (w/v) in water and 0.02% (w/v) in phosphate buffered saline, causing hemolysis of sheep red blood cells at concentrations of 25 μg/ml or greater, and containing the monosaccharides terminal rhamnose, terminal arabinose, terminal apiose, terminal xylose, 4-rhamnose, terminal glucose, terminal galactose, 2-fucose, 3-xylose, 3,4-rhamnose, and 2,3-glucuronic acid.

In one embodiment, the present invention provides pharmaceutical compositions, e.g., vaccine compositions, comprising a synergistic combination of RC-529 and QS-21. This adjuvant combination can be said to act in a synergistic fashion because it has an effect that is larger than the sum of the separate effects of each adjuvant. For example, this adjuvant system can synergistically enhance the immune responses to a co-administered antigen. The synergy between these two adjuvant-types for CTL induction has important implications for the use of recombinant molecules as vaccines for induction of CTL-mediated immunity.

Induction of CTL is typically seen when a target antigen is synthesized intracellularly (e.g. in infections by viruses, intracellular bacteria, or in tumors), because peptides generated by proteolytic breakdown of the antigen can enter the appropriate processing pathway, leading to presentation in association with class I molecules on the cell membrane. However, in general, pre-formed soluble antigen does not reach this processing and presentation pathway, and does not elicit class I restricted CTL. Therefore conventional non-living vaccines, while eliciting antibody and T helper responses, are not generally effective in inducing CTL-mediated immunity. The adjuvant combinations herein overcome this limitation of vaccines based on recombinant proteins, and induce a wider spectrum of immune responses.

The disclosed adjuvant systems comprising RC-529 and QS-21 can also enhance interferon (IFN) gamma production. IFN-gamma secretion is associated with protective responses against intracellular pathogens, including parasites, bacteria and viruses. Activation of macrophages by IFN-gamma enhances intracellular killing of microbes and increases expression of Fc receptors. Direct cytotoxicity may also occur, especially in synergism with lymphotoxin (another product of TH1 cells). IFN-gamma is also both an inducer and a product of NK cells, which are major innate effectors of protection. TH1 type responses, either through IFN-.gamma. or other mechanisms, provide preferential help for IgG2a immunoglobulin isotypes.

Thus, the adjuvant systems of the invention are particularly advantageous in making and using vaccine compositions to induce active immunity towards antigens in mammals, preferably in humans. Vaccine preparation is a well developed art and general guidance in the preparation and formulation of vaccines is readily available from any of a variety of sources. One such example is New Trends and Developments in Vaccines, edited by Voller et al., University Park Press, Baltimore, Md., U.S.A. 1978.

The optimal amount of a given vaccine composition to be administered will vary, however such information is easily determined using standard procedures. For example, the immunogenic activity of a given amount of a vaccine composition of the present invention can be determined by monitoring the increase in titer of antibody against the antigen used in the vaccine composition (Dalsgaard, K. Acta Veterinia Scandinavica 69:I-40 (1978)). Another common method involves injecting CD-1 mice intradermally with various amounts of a vaccine composition, later harvesting sera from the mice and testing for anti-immunogen antibody, e.g., by ELISA. These and other similar approaches will be apparent to the skilled artisan.

The adjuvant system of the present invention exhibits strong adjuvant effects when administered over a wide range of dosages and a wide range of ratios. The ratio of QS-21:RC-529 will typically be on the order of 1:10 to 10:1;

more typically about 1:5 to 5:1 and often substantially 1:1. Typically for human administration, QS-21 RC-529 will be present in a vaccine composition in the range 1 μg–100 μg, preferably 10 μg–50 μg per dose.

The amount of antigenic protein in each vaccine dose is generally selected as an amount which induces an immunoprotective response without significant adverse side effects in typical vaccines. Such amount will vary depending upon which specific immunogen is employed and how it is presented. Generally, it is expected that each dose will comprise about 1–1000 μg of protein, most typically about 2–100 μg, preferably about 5–50 μg. Of course, the dosage administered may be dependent upon the age, weight, kind of concurrent treatment, if any, and nature of the antigen administered.

The antigen can be derived and/or isolated from essentially any desired source. By way of illustration, the antigens can be derived from viral sources, such as influenza virus, feline leukemia virus, feline immunodeficiency virus, HIV-1, HIV-2, rabies, measles, hepatitis B, or hoof and mouth disease viruses. Illustrative antigens can also be derived from bacterial sources, such as anthrax, diphtheria, Lyme disease, malaria, tuberculosis, Leishmaniasis, *T. cruzi, Ehrlichia, Candida* etc., or from protozoans such as *Babeosis bovis* or *Plasmodium*. The antigen(s) will typically be comprised of natural or synthetic amino acids, e.g., in the form of peptides, polypeptides, or proteins, can be comprised of polysaccharides, or can be mixtures thereof. Illustrative antigens can be isolated from natural sources, synthesized by means of solid phase synthesis, or can be obtained by way of recombinant DNA techniques.

In another embodiment, the adjuvant system of the present invention is used in prophylactic and/or therapeutic cancer vaccine compositions. Cancer cells often have distinctive antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, the adjuvant systems described herein can be utilized. As a result, exogenous proteins can enter the pathway for processing endogenous antigens, leading to the production of cytolytic or cytotoxic T cells (CTL). This adjuvant effect facilitates the production of antigen specific CTLs which seek and destroy those tumor cells carrying on their surface the tumor antigen(s) used for immunization. Illustrative cancer types for which this approach can be used include prostate, colon, breast, ovarian, pancreatic, brain, head and neck, melanoma, leukemia, lymphoma, etc.

In another embodiment of the invention, the adjuvant system of the present invention can be administered alone, i.e., without a co-administered antigen, to potentiate the immune system for treatment of chronic infectious diseases, especially in immune compromised patients. Illustrative examples of infectious diseases for which this approach may be employed for therapeutic or prophylactic treatment can be found in U.S. Pat. No. 5,508,310. Potentiation of the immune system in this way can also be useful as a preventative measure to limit the risks of nosocomial and/or post-surgery infections.

In another embodiment, the antigen present in the vaccine compositions is not a foreign antigen, rather it is a self antigen, e.g., the vaccine composition is directed toward an autoimmune disease such as type 1 diabetes, conventional organ-specific autoimmune diseases, neurological diseases, rheumatic diseases, psoriasis, connective tissue diseases, autoimmune cytopenias, and other autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, antireceptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjorgren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts.

In one embodiment, the adjuvant system described herein is used in the preparation of DNA-based vaccine compositions. Illustrative vaccines of this type contain DNA encoding one or more polypeptide antigens, such that the antigen is generated in situ. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In one preferred embodiment, the DNA is introduced using a viral expression system (e.g., vaccinia or other pox virus, retrovirus, or adenovirus), which typically involves the use of a non-pathogenic (defective), replication competent virus. Illustrative systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. Alternatively, the DNA may be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads that are efficiently transported into the cells. It will be apparent that a vaccine may comprise both a polynucleotide and a polypeptide component if desired.

Moreover, it will be apparent that a vaccine may contain pharmaceutically acceptable salts of the desired polynucleotide, polypeptide and/or carbohydrate antigens. For example, such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will typically vary depending on the desired mode of administration. Compositions of the present invention may be formulated for any appropriate manner of administration, including for example, topical, oral, nasal, intravenous, intracranial, intraperitoneal, intradermal, subcutaneous or intramuscular administration. For parenteral administration, such as subcutaneous injection, the carrier will often comprise water, saline, alcohol, a fat, a wax or a buffer. For oral administration, the above carriers are often used, or a solid carrier such as mannitol, lactose, starch, magnesium stearate, sodium saccharine, talcum, cellulose, glucose, sucrose, and magnesium carbonate, can also be employed. Biodegradable microspheres (e.g., polylactate polyglycolate) may also be employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252, the disclosures of which are incorporated herein by reference in their entireties. Modified hepatitis B core protein carrier systems are also suitable, such as those described in WO/99 40934, and references cited therein, all incorporated herein by reference. One may also employ a carrier comprising particulate-protein complexes, e.g., as described in U.S. Pat. No. 5,928,647, the disclosure of which is incorporated herein by reference in its entirety, which are capable of inducing a class I-restricted cytotoxic T lymphocyte responses in a host.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual. vaccine delivery, especially for pediatric applications, or for applications traditionally requiring numerous injections over a prolonged period of time, such as with allergy desensitization therapies.

The vaccine compositions can also comprise buffers (e.g., neutral buffered saline, phosphate buffered saline or phosphate buffers w/o saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. The compositions can also be encapsulated within liposomes using well known technology.

For certain applications, an aqueous formulation of RC-529 and QS-21 provides unexpectedly strong adjuvant activity. Therefore, in one embodiment, the vaccine composition is an aqueous formulation comprising one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE).

Typically, a surfactant:adjuvant molar ratio in an aqueous formulation will be from about 10:1 to about 1:10, more typically from about 5:1 to about 1:5, however any effective amount of surfactant may be used in an aqueous formulation to best suit the specific objectives of interest.

In another embodiment, the composition is an emulsion, such as a water-in-oil emulsion or an oil-in water emulsion. Such emulsions are generally well known to those skilled in this art.

The adjuvant system of the present invention can be employed as the sole adjuvant system, or alternatively, can be administered together with other adjuvants or immunoeffectors. By way of illustration, such adjuvants can include oil-based adjuvants (for example, Freund's Complete and Incomplete), liposomes, mineral salts (for example, AlK$(SO_4)_2$, AlNa$(SO_4)_2$, AlNH$_4(SO_4)$, silica, alum, Al(OH)$_3$, Ca$_3$(PO$_4$)$_2$, kaolin, and carbon), polynucleotides (for example, poly IC and poly AU acids), polymers (for example, non-ionic block polymers, polyphosphazenes, cyanoacrylates, polymerase-(DL-lactide-co-glycoside), among others, and certain natural substances (for example, lipid A and its derivatives, wax D from *Mycobacterium tuberculosis*, as well as substances found in *Corynebacterium parvum, Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods well known to those skilled in the art. When obtained from recombinant sources, the adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3,3'-dicarboxylic acid and 4-nitro-2-aminobenzoic acid (See Sela, M., Science 166:1365–1374 (1969)) or glycolipids, lipids or carbohydrates.

In one embodiment, the adjuvant system is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

For example, additional adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Other illustrative adjuvants that can be included in the vaccine compositions include Montanide ISA 720 (Seppic, France), SAF (Chiron, Calif., United States), ISCOMS (CSL), MF-59 (Chiron), Detox (Corixa, Hamilton, Mont.).

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., Vaccine 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

EXAMPLES

The following examples are offered to illustrate, but not to limit the claimed invention.

This example demonstrates synergy between QS-21 adjuvant when combined with RC-529 adjuvant, such that greater levels of CTL activity and interferon-gamma secretion are induced with the combination than by either adjuvant alone, or in the absence of adjuvant. This experiment employed a recombinant polypeptide antigen from M. tuberculosis, referred to as rDPV, to immunize C57BL/6 mice subcutaneously. Briefly, groups of four female 6–8 week old C57BL/6 mice were immunized subcutaneously with 5 ug rDPV combined with 10 ug 529, 10 ug QS-21 or a combination the two, formulated in both aqueous (AF) and oil emulsion (SE) formulations. The RC-529 aqueous formulations comprise DPPC surfactant, in which the DPPC:529 molar ratio is about 8:1. Additional mice received the equivalent dose of antigen formulated in adjuvant combinations comprising MPL (Corixa Corp., Seattle, Wash.) and QS-21 in aqueous and oil emulsion formulations. Control mice were immunized with PBS. Immunizations were performed at weeks 0,3 and 7, and spleens were harvested 2 weeks later. Single cell suspensions of splenocytes were stimulated in vitro with EL-4 cells stably transduced to express DPV. Thirteen days later these cells were assayed for CTL activity against EL-4-DPV by standard chromium release techniques. Additional fresh splenocytes were stimulated in vitro with 5 ug/ml rDPV and supernatants were harvested 3 days later and assayed for IFN-g by ELISA. The results of the above experiments are summarized in Tables 1 and 2 below.

Table 1 illustrates interferon -gamma secretion from splenocytes of immunized mice following stimulation in vitro with 5 μg/ml recombinant DPV protein. Concentration of IFN-γ was measured in 3-day supernatants by ELISA, and is expressed as mean concentration for groups of four mouse spleens.

TABLE 1

| Immunogen | Interferon-gamma secretion (pg/ml) |
|---|---|
| rDPV | 723.50 |
| rDPV + MPL-AF | 702.34 |
| rDPV + MPL-SE | 2861.04 |
| rDPV + 529-AF | 538.75 |
| rDPV + 529-SE | 14242.53 |
| rDPV + QS-21 | 831.73 |
| rDPV + QS-21 + MPL-AF | 25301.44 |
| rDPV + QS-21 + MPL-SE | 2896.08 |
| rDPV + QS-21 + 529-AF | 34294.48 |
| rDPV + QS-21 + 529-SE | 13275.99 |
| saline | 911.90 |

Table 2 shows CTL activity of splenocytes stimulated for 13 days in vitro with EL-4 cells stably expressing DPV. Percent specific lysis (chromium release) is expressed as the mean of four mouse spleens per group, with background lysis against EL-4 cells. subtracted, at an effector to target ratio of 100:1.

TABLE 2

| Immunogen | % Specific Lysis |
|---|---|
| rDPV | 8.1 |
| rDPV + MPL-AF | 10.5 |
| rDPV + MPL-SE | 13.6 |
| rDPV + 529-AF | 10.4 |
| rDPV + 529-SE | 14.0 |
| rDPV + QS-21 | 9.7 |
| rDPV + MPL-AF + QS-21 | 31.8 |
| rDPV + MPL-SE + QS-21 | 16.2 |
| rDPV + 529-AF + QS-21 | 32.7 |
| rDPV + 529-SE + QS-21 | 13.2 |
| Saline | 11.9 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An aqueous immunostimulant composition comprising QS-21 and 2-[(R)-3-Tetradecanoyloxytetradecanoylamino]ethyl-2-Deoxy-4-O-phosphono-3-O-[(R)-3-tetradecanoyloxytetradecanoyl]-2-[(R)-3-tetradecanoyloxytetradecanoylamino]-β-D-glucopyranoside or its triethylammonium salt.

2. The composition of claim 1, wherein the aqueous formulation comprises one or more surfactants.

3. The composition of claim 1, wherein the aqueous formulation comprises one or more phospholipid surfactant.

4. The composition of claim 3, wherein the surfactant is selected from the group consisting of diacyl phosphatidyl glycerols, diacyl phosphatidyl cholines, diacyl phosphatidic acids, and diacyl phosphatidyl ethanolamines.

5. The composition of claim 3, wherein the surfactant is selected from the group consisting of dimyristoyl phosphatidyl glycerol (DPMG), dipalmitoyl phosphatidyl glycerol (DPPG), distearoyl phosphatidyl glycerol (DSPG), dimyristoyl phosphatidylcholine (DPMC), dipalmitoyl phosphatidylcholine (DPPC), distearoyl phosphatidylcholine (DSPC); dimyristoyl phosphatidic acid (DPMA), dipalmitoyl phosphatidic acid (DPPA), distearoyl phosphatidic acid (DSPA); dimyristoyl phosphatidyl ethanolamine (DPME), dipalmitoyl phosphatidyl ethanolamine (DPPE) and distearoyl phosphatidyl ethanolamine (DSPE).

6. The composition of claim 1, further comprising at least one antigen.

7. The composition of claim 6, wherein the antigen is derived from the group consisting of Herpes Simplex Virus type 1, Herpes Simplex virus type 2, Human cytomegalovirus, HIV, Hepatitis A, B, C or E, Respiratory Syncytial virus, human papilloma virus, Influenza virus, *Tuberculosis, Leishmaniasis, T. Cruzi, Ehrlichia, Candida, Salmonella, Neisseria, Borrelia, Chlamydia, Bordetella, Plasmodium* and *Toxoplasma*.

8. The composition of claim 6, wherein the antigen is a human tumor antigen.

9. The composition of claim 8, wherein the human tumor antigen is derived from a prostate, colon, breast, ovarian, pancreatic, brain, head and neck, melanoma, leukemia or lymphoma cancer.

10. The composition of claim 6, wherein the antigen is a self antigen.

11. The composition of claim 10, wherein the self antigen is an antigen associated with an autoimmune disease.

12. The composition of claim 11, wherein the autoimmune disease is type 1 diabetes, multiple sclerosis, myasthenia gravis, rheumatoid arthritis or psoriasis.

13. The composition of claim 1, wherein the QS-21 and 2-[(R)-3-Tetradecanoyloxytetradecanoylamino]ethyl-2-Deoxy-4-O-phosphono-3-O-[(R)-3-tetradecanoyloxytetradecanoyl]-2-[(R)-3-tetradecanoyloxytetradecanoylamino]-β-D-glucopyranoside or its triethylammonium salt are administered at a ratio of QS21: glucopyranoside or salt from about 1:10 to about 10:1.

14. The composition of claim 1, wherein the QS-21 and 2-[(R)-3-Tetradecanoyloxytetradecanoylamino]ethyl-2-Deoxy-4-O-phosphono-3-O-[(R)-3-tetradecanoyloxytetradecanoyl]-2-[(R)-3-tetradecanoyloxytetradecanoylamino]-β-D-glucopyranoside or its triethylammonium salt are administered at a ratio of QS21: glucopyranoside or salt from about 2.5:1 to about 1:2.5.

15. A method of enhancing the immune response in a mammal which comprises administering to the mammal a composition according to any of claims 1, 2–5, 13 or 14.

16. A method of enhancing the immune response in a mammal to an antigen which comprises administering to the mammal a composition according to any of claims 1, 2–5, 13 or 14 in combination with an antigen.

17. The method of claim 16, wherein the antigen is derived from the group consisting of Herpes Simplex Virus type 1, Herpes Simplex virus type 2, Human cytomegalovirus, HIV, Hepatitis A, B, C or E, Respiratory Syncytial virus, human papilloma virus, Influenza virus, *Tuberculosis, Leishmaniasis, T. Cruzi, Ehrlichia, Candida, Salmonella, Neisseria, Borrelia, Chlamydia, Bordetella, Plasmodium* and *Toxoplasma*.

18. The method of claim 16, wherein the antigen is a human tumor antigen.

19. The method of claim 18, wherein the human tumor antigen is derived from a prostate, colon, breast, ovarian, pancreatic, brain, head and neck, melanoma, leukemia or lymphoma cancer.

20. The method of claim 16, wherein the antigen is a self antigen.

21. The method of claim 20, wherein the self antigen is an antigen associated with an autoimmune disease.

22. The method of claim 21, wherein the autoimmune disease is type 1 diabetes, multiple sclerosis, myasthenia gravis, rheumatoid arthritis or psoriasis.

23. An immunostimulant composition comprising QS-21 and 2-[(R)-3-Tetradecanoyloxytetradecanoylamino]ethyl-2-Deoxy-4-O-phosphono-3-O-[(R)-3-tetradecanoyloxytetradecanoyl]-2-[(R)-3-tetradecanoyloxytetradecanoylamino]-β-D-glucopyranoside or its triethylammonium salt in an aqueous formulation comprising one or more phospholipid surfactants selected from the group consisting of dimyristoyl phosphatidyl glycerol (DPMG), dipalmitoyl phosphatidyl glycerol (DPPG), distearoyl phosphatidyl glycerol (DSPG), dimyristoyl phosphatidylcholine (DPMC), dipalmitoyl phosphatidylcholine (DPPC), distearoyl phosphatidylcholine (DSPC); dimyristoyl phosphatidic acid (DPMA), dipalmitoyl phosphatidic acid (DPPA), distearoyl phosphatidic acid (DSPA); dimyristoyl phosphatidyl ethanolamine (DPME), dipalmitoyl phosphatidyl ethanolamine (DPPE) and distearoyl phosphatidyl ethanolamine (DSPE).

24. The composition of claim 23, further comprising at least one antigen.

25. A method of enhancing the immune response in a mammal which comprises administering to the mammal a composition according to claim 23.

26. A method of enhancing the immune response in a mammal to an antigen which comprises administering to the mammal a composition according to claim 23 in combination with antigen.

27. The composition of claim 1, wherein the QS-21 and 2-[(R)-3-Tetradecanoyloxytetradecanoylamino]ethyl-2-Deoxy-4-O-phosphono-3-O-[(R)-3-tetradecanoyloxytetradecanoyl]-2-[(R)-3-tetradecanoyloxytetradecanoylamino]-β-D-glucopyranoside or its triethylammonium salt are administered at a ratio of QS21: glucopyranoside or salt about 1:1.

* * * * *